United States Patent [19]

Kakibayashi et al.

[11] Patent Number: 5,475,218
[45] Date of Patent: Dec. 12, 1995

[54] INSTRUMENT AND METHOD FOR 3-DIMENSIONAL ATOMIC ARRANGEMENT OBSERVATION

[75] Inventors: Hiroshi Kakibayashi, Nagareyama; Yasuhiro Mitsui, Fuchu; Hideo Todokoro, Nishitama; Katsuhiro Kuroda, Hachiouji, all of Japan

[73] Assignee: Hitachi, Ltd., Tokyo, Japan

[21] Appl. No.: 79,273

[22] Filed: Jun. 21, 1993

Related U.S. Application Data

[62] Division of Ser. No. 882,970, May 14, 1992, Pat. No. 5,278,408.

[30] Foreign Application Priority Data

May 15, 1991 [JP] Japan .................. 3-110126

[51] Int. Cl.$^6$ ........................................ H01J 27/26
[52] U.S. Cl. .......................................... 250/311
[58] Field of Search ............................. 250/311, 306, 250/307, 492.2, 392, 310

[56] References Cited

U.S. PATENT DOCUMENTS

| | | | |
|---|---|---|---|
| 4,068,123 | 1/1978 | Kokubo | 250/311 |
| 4,724,320 | 2/1988 | Ino et al. | 250/310 |
| 4,866,273 | 9/1989 | Kobayashi et al. | 250/311 |

FOREIGN PATENT DOCUMENTS

| | | |
|---|---|---|
| 0348992 | 1/1990 | European Pat. Off. . |
| 0472235A1 | 2/1992 | European Pat. Off. . |
| 62096807 | 10/1985 | Japan . |
| 1211849 | 11/1989 | Japan . |

OTHER PUBLICATIONS

*Philips Technical Review*, "The Microprocessor–Controlled CM12/STEM Scanning–Transmission Electron Microscope", U. Gross, et al., 43 (1987) Nov., No. 10, Eindhoven, The Netherlands.

*Primary Examiner*—Paul M. Dzierzynski
*Assistant Examiner*—Kiet T. Nguyen
*Attorney, Agent, or Firm*—Antonelli, Terry, Stout & Kraus

[57] ABSTRACT

3-dimensional observation is carried out on the atomic arrangement and atomic species in a thin-film specimen at an atomic level in order to clarify the existence states of defects and impure atoms in the crystals. For that purposes, the present invention provides an instrument and a method for 3-dimensional observation of an atomic arrangement which are implemented by a system comprising a scanning transmission electron microscope equipped with a field emission electron gun operated at an acceleration voltage of greater than 200 kV, a specimen goniometer/tilting system having a control capability of the nanometer order, a multi-channel electron detector and a computer for executing software for controlling these components and 3-dimensional image-processing software. Point defects and impure atoms, which exist in joint interfaces and contacts in a ULSI device, can thereby be observed. As a result, the causes of bad devices such as current leak and poor voltage resistance can be analyzed at a high accuracy.

8 Claims, 4 Drawing Sheets

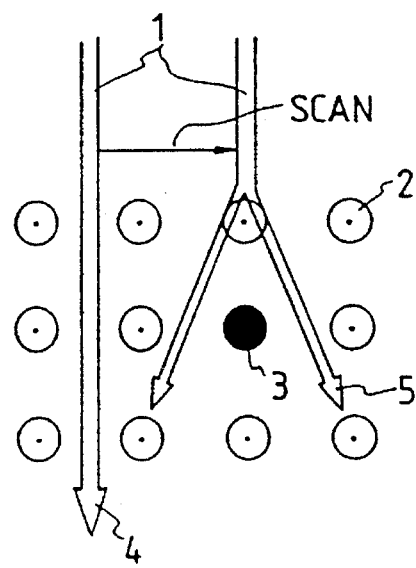 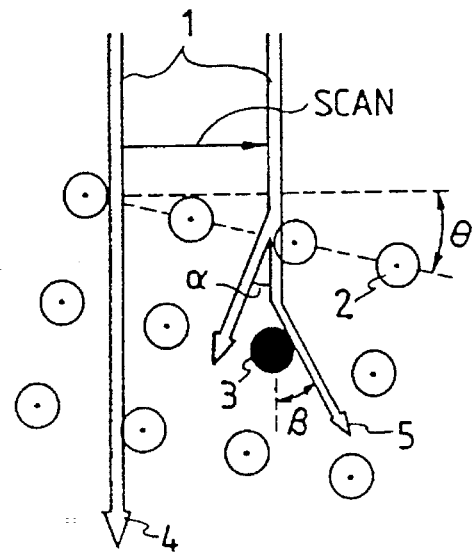
FIG. 1(a)   FIG. 1(b)
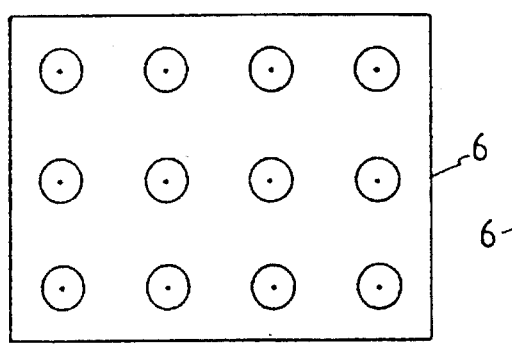 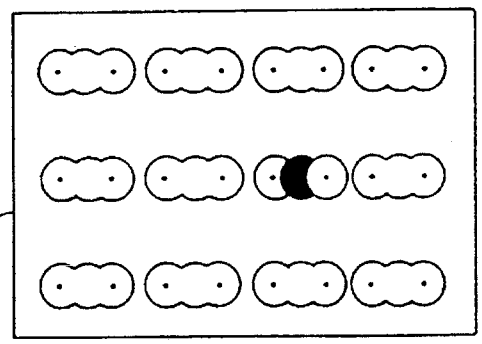

INSTRUMENT AND METHOD FOR 3-DIMENSIONAL ATOMIC ARRANGEMENT OBSERVATION

This is a divisional of application Ser. No. 07/882,970, filed May 14, 1992, now U.S. Pat. No. 5,278,408.

BACKGROUND OF THE INVENTION

The present invention relates to an instrument and method for the observation of point defects, impure atoms and their clusters which exist at joint interfaces and contacts in an integrated device formed into a layered structure such as a memory or fast-calculation device.

As described in Proc. Mat. Res. Soc. Symp. Vol. 183 (Materials Research Society, San Francisco, 1990) p. 55, the conventional electron microscope can be used for inferring a 3-dimensional atomic arrangement from several electron microscope images observed from different directions. In addition, a technique for obtaining a 2-dimensional image of a 3-dimensional atomic structure is disclosed in Japanese Patent Laid-open No. 61-78041.

SUMMARY OF THE INVENTION

With the conventional techniques mentioned above, it is necessary to prepare a large number of thinned pieces having a thickness of the order of several nm by cutting a specimen in various directions. In this case, if a target structure in the specimen has an infinitesimal size of the order of nanometers, it is impossible to cut the structure into a plurality of pieces and, thus, impossible to carry out 3-dimensional observation. Even if the target structure is large enough to allow the thinned pieces to be prepared, only part of the target structure is contained in such a piece so that a lot of information is found missing when constructing a 3-dimensional structure based on the electron microscope images of the pieces. In addition, since the observer has to infer a 3-dimensional structure while taking the relation between observation directions and their electron microscope images of thinned pieces, the technique results in very inadequate precision. The accuracy of the observation directions is effected by errors in the angle setting when specimen pieces are cut out and inclinations of the specimen pieces set on the specimen holder of the electron microscope. It is difficult to make the observation conditions by electron microscopes completely uniform for all the specimen pieces. The resulting errors thus give rise to variations in image contrast. An inference image formed by diffracted electrons, or a lattice image, varies depending upon, among other things, the thickness of the specimen and electron diffraction conditions. In addition, even though information on the atomic arrangement can be obtained from a lattice image, it is difficult to identify the atomic species of impurities and point defects.

In addition, it is disclosed in Japanese Patent Laid-open No. 61-78041 that the electron incidence direction to the specimen surface is fixed and all reflected characteristic X-rays generated in the specimen can be obtained by changing the direction of detection. Information on the structure of a 3-dimensional atomic arrangement close to the surface is thereby obtained. Nevertheless, the obtained information is limited to one to two atomic layers on the surface due to the use of all the reflected characteristic X-rays. In addition, since the characteristic X-rays are generated from a region of the micron order, it is impossible to obtain high resolution at an atomic level. It is thus extremely difficult to obtain a 3-dimensional atomic arrangement in the bulk with a high resolution at an atomic level.

It is an object of the present invention to obtain a 3-dimensional atomic arrangement and atomic species in the bulk with a high resolution at an atomic level using only a single thin-film specimen and, thus, to allow a 3-dimensional atomic structure to be analyzed accurately in a short period of time.

In order to achieve the object described above, a system comprising a scanning transmission electron miroscope, a specimen goniometer/tilting system, a multi-channel electron detector and a computer was built. The scanning transmission electron microscope includes a unit for radiating an electron beam having a diameter equal to or smaller than the size of one to two atoms. The specimen goniometer/tilting system can be controlled to move a specimen by a distance of the order of nanometers. The multi-channel electron detector allows the range of detection angles of scattered electrons to be arbitrarily set. The computer is used for executing software for controlling the electron microscope and softwares for image processing. The system is thus equipped with facilities for observing a 3-dimensional structure. To speak in more concrete terms, the system is characterized in that some projection images of atomic arrangement are obtained within an angular increment range θ from a predetermined inclination angle. While rotating the specimen over an angle in a range smaller than the angular increment θ, n images of 2-dimesional atomic-arrangement are produced. Note that within the angular range in which the projection image of atomic arrangement is obtained, the so-called channeling phenomenon must occur at least once. In addition, the angular increment θ is equal to $\tan^{-1}(d/t)$, where d is the distance from an atom to an adjacent one in the specimen and t is the thickness of the specimen. From the n images of 2-dimensional atomic-arrangement obtained as such, atomic coordinates with rough precision and atomic species are identified. Next, a 2-dimensional atomic-arrangement image is simulated by the informations.

The simulated image is then compared to the 2-dimensional atomic-arrangement images actually measured. Atomic coordinates and atomic species with high accuracy are obtained as both the images match each other. The accurate atomic coordinates and atomic species are used to display a 3-dimensional atomic-arrangement image.

Accordingly, not only is a 3-dimensional atomic arrangement observed, but a structural analysis can also be performed as well using the same system.

A thin-film specimen is observed using the scanning transmission electron microscope using an electron beam with a diameter equal to or smaller than the size of one to two atoms. The observation can result in an atomic-arrangement image. By observing the specimen while varying its inclination by means of the specimen goniometer/tilting system, atomic-arrangement images from various directions can be obtained. By applying image processing to the atomic-arrangement images obtained for various inclination angles, a 3-dimensional atomic arrangement of the specimen can be constructed and atomic species can be identified from an analysis of a relation between the detection-angle ranges of scattered electrons used in the imaging and the degrees of the image contrast.

BRIEF DESCRIPTION OF THE DRAWINGS (FIG. 1 is an explanatory view showing the principle of image formation using an electron beam with a diameter equal to or smaller than the size of one to two atoms.) FIG. 1(a) shows states of transmission and scattering electron beams and an electron-microscope image when electron beam is parallel to the direction of atomic columns. FIG. 1(b) shows states of transmission and scattering electron beams and an electron-microscope image when electron beam has an incident angle θ to the direction of the atomic columns.

DETAILED DESCRIPTION OF THE PREFERRED EMBODIMENTS

Figure 5:
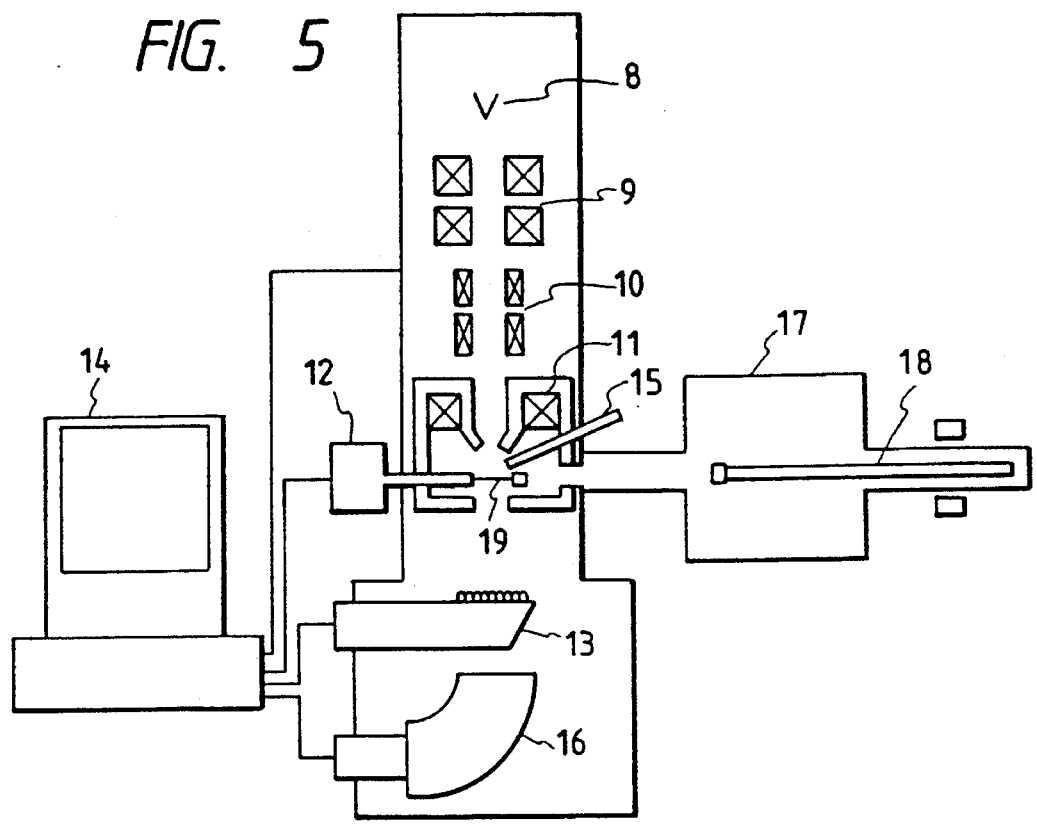
FIG. 5 is a diagram showing an overall structure of an embodiment according to the present invention.

Referring to the diagrams described briefly above, embodiments according to the present invention are explained as follows. FIG. 5 is a diagram showing a basic configuration of an electron-microscope apparatus used in the embodiments according to the present invention. As shown in the figure, the apparatus comprises a field emission electron gun 8, condenser lenses 9, electron deflector coils 10, object lenses 11, a specimen goniometer/tilting system 12, an electron detector 13, a computer 14 for executing control and image-processing software, an X-ray detector 15, an energy analyzer 16, a specimen preparation room 17 and a specimen transfer system 18. In order to generate an electron beam with a diameter equal to or smaller than the size of one to two atoms, an acceleration voltage of at least 200 kV is applied to the field emission electron gun 8 and magnetic lenses for illumination with small aberration are employed. A specimen 19 is scanned by the beam deflecting/scanning coil 7 by applying an electron beam to the specimen 19. The electron detector 13 has a multi-channel typed matrix of a plurality of photosensitive devices. The intensities of electrons scattered and transmitted by the specimen 19 can be measured by identifying relations between the addresses of the photosensitive devices in the matrix and the scattering angles and directions of the electrons. Even though CCD photosensitive devices are typically employed in the electron detector 13, photosensitive devices of other types with high sensitivity can also be used as well. The specimen goniometer/tilting system 12 comprises a step motor and a goniometer which are controlled by the computer 14. This allows the inclination of the specimen 19 to be adjusted in the milliradian order. So, the positional aberration is compensated in the nanometer order. The computer 14 executes the control and image-processing software, allowing intensities and distribution of electrons measured by the electron detector 13 to be input and stored into memory in synchronization with the scanning operation of the incident electron beam. In addition, the computer 14 is also capable of carrying out a variety of image processings.

Figure 2:
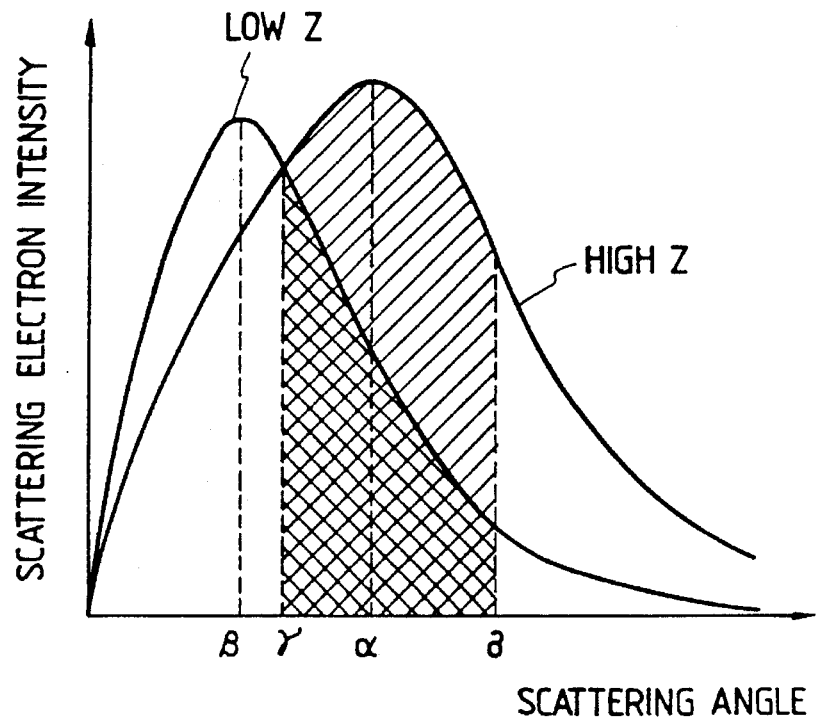
FIG. 2 is an explanatory view showing relations between the scattering electron intensity and the scattering angle for atoms with low and high atomic numbers.
Figure 3:
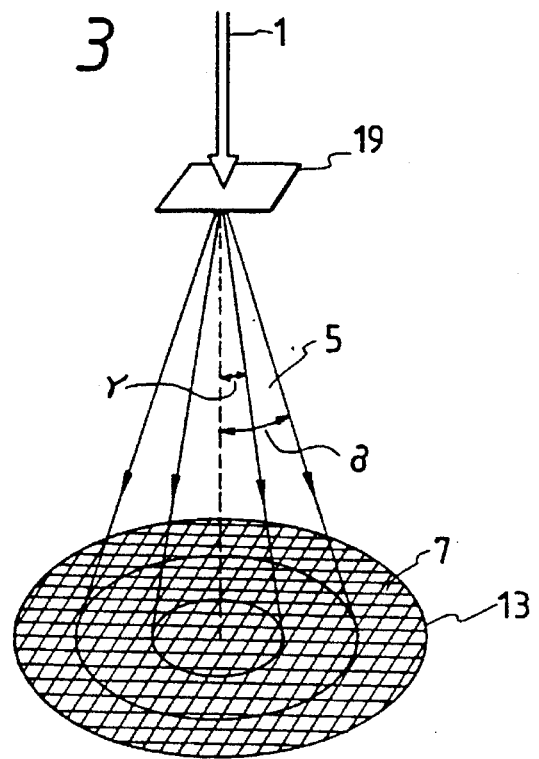
FIG. 3 is an explanatory view for measurement of scattering electrons by a multi-channel electron detector in a scattering angle between γ and δ.
Figure 6:
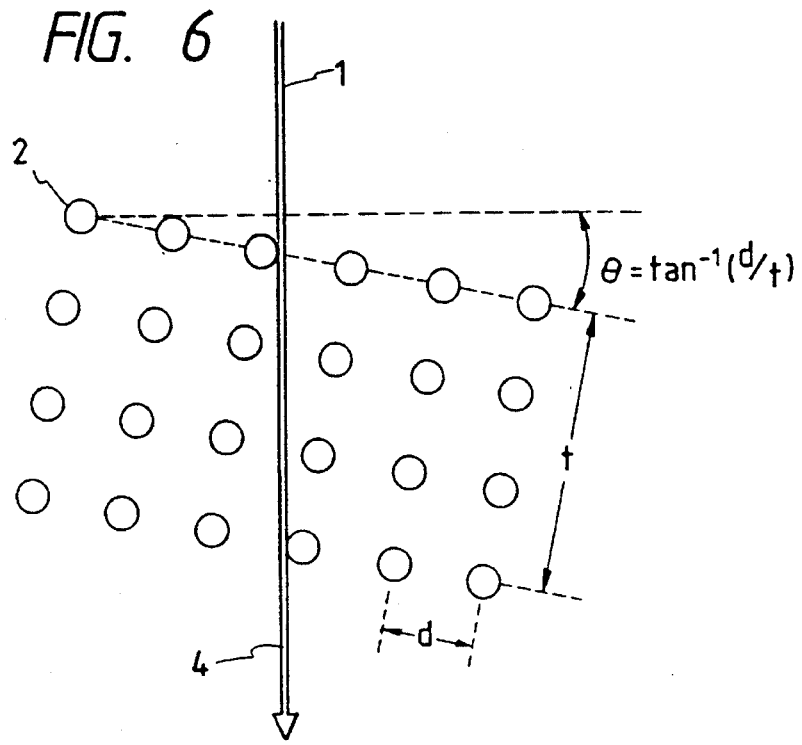
FIG. 6 is an explanatory diagram showing a relation between the angular increment (θ) of the specimen, the distance from an atom to an adjacent one (d) and the thickness of the specimen (t).

Next, a step of observing a 3-dimensional atomic arrangement according to the present invention is described. FIG. 1 shows interaction between an atom 2 constituting the thin-film specimen 19 and incident an electron beam 1 having a diameter equal to or smaller than the size of one to two atoms. FIG. 1(a) shows a case in which the incident electron beam 1 is parallel to the direction of the atomic columns of the thin-film specimen 19. In this case, an electron incident beam 1 between two adjacent atomic columns is transmitted through by a channelling phenomenon without being scattered by the atoms 2. Note that the channelling phenomenon is a phenomenon in which an electron beam 1 is passed through. An incident electron beam 1 hitting an atomic column is scattered by the first atom 2 on the atomic column. By measuring the intensity of a transmitted or scattered electron 4 or 5 in synchronization with the scanning operation of the incident electron beam 1 by means of the electron detector 13, a projection image of atomic arrangement 6 can thus be observed. Next, the thin-film specimen 19 is inclined to form an angle θ with the incident electron beams 1. As shown in FIG. 6, the angle θ is set to a value smaller than $\tan^{-1}(d/t)$, where d is the distance from an atom to an adjacent one on the thin-film specimen 19 and t is the thickness of the thin-film specimen 19. Though the gap between two adjacent atomic columns as seen from the incident direction of the electron beams 1 becomes smaller, a channelling electron exists. As shown in FIG. 1(b), the projection image of the arrangement 6 corresponds to a projection image viewed from an inclined direction forming the angle θ with the atomic columns. In this case, the view of an impure atom 3 is different from that of FIG. 1(a). That is to say, the impure atom 3 in FIG. 1(a) is not visible because it is shadowed by an atom 2 located right above it. In the case shown in FIG. 1(b), however, the different atom 3 is visible. Accordingly, the incident electron beam 1 is scattered also by the impure atom 3. In general, relations between the scattering angle and the intensity of a scattered electron are shown in FIG. 2. As shown in the figure, the scattered electron intensity is distributed among the scattering angles with a peak located at certain scattering-angle values. The distribution curves are flatter for high scattering-angle values. The distribution curves are also different from each other depending upon the atomic number (Z). The larger the value of the atomic number (Z), the more the distribution curve is shifted to the side of large scattering-angle values. Accordingly, a scattering angle β for the peak intensity of electrons 5 scattered by the impure atom 3 is different from a scattering angle α for the peak intensity of electrons scattered by a surrounding atom 2. In this case, the atom 2 has a greater atomic number than the impure atom 3. Taking the distribution shown in FIG. 2 into consideration, the detection angle range of the scattered electrons 5 used in the imaging by the electron detector 13 is set between angles γ and δ shown in the figure. FIG. 3 shows a state of operation of the electron detector 13 for the detection angle range between γ and δ. As shown in the figure, the electron detector 13 has a multi-channel matrix configuration which comprises a plurality of photosensitive devices 7, each photosensitive device has a size of several micrometers or less.

When the incident electron beam 1 hits the specimen 19, electrons 5 are scattered at a variety of scattering angles, arriving at the electron detector 13. Only electrons with scattering angles between γ and δ are used for creating a projection image of atomic arrangement 6. That is to say, only the intensities of scattered electrons 5, which are detected by photosensitive devices 7 located between two concentric circles corresponding to the scattering angles γ and δ, are measured in synchronization with the scanning operation of the incident electron beam 1. The range of detection angles is set by specifying the addresses of the photosensitive devices 7 with the computer 14. With such measurement, the difference in contrast between atoms on the projection image can be recognized. In this case, the atom 2 is bright whereas the different atom 3 is dark. By embracing the same principle, the difference can still be recognized even if a vacancy exists at the position of the impure atom 3. Information on distribution of scattered electron intensities for various atoms are stored in the computer 14. Accordingly, the detection angle ranges for the various atoms can be set in the electron detector 13. The various atoms can thus be distinguished from each other based on differences in image contrast between them. In addition, since the specimen goniometer/tilting system 12 allows the inclination angle of the specimen 19 to be controlled in the milliradian order, an inclination angle can be set at the condition of the channelling-phenomenon. Moreover, the position of the specimen 19 can be controlled using the computer 14 so that the target of observation on the specimen 19 is always located at the center of the observation area. The computer-based control is carried out by finding the amount of aberration in the position of the specimen 19, that results with the specimen 19 inclined, using the image processing. By continuously observing images while varying the inclination angle and storing image data in the computer 14, the projection images of atomic arrangement 6 observed from a variety of directions can be obtained.

Figure 4:
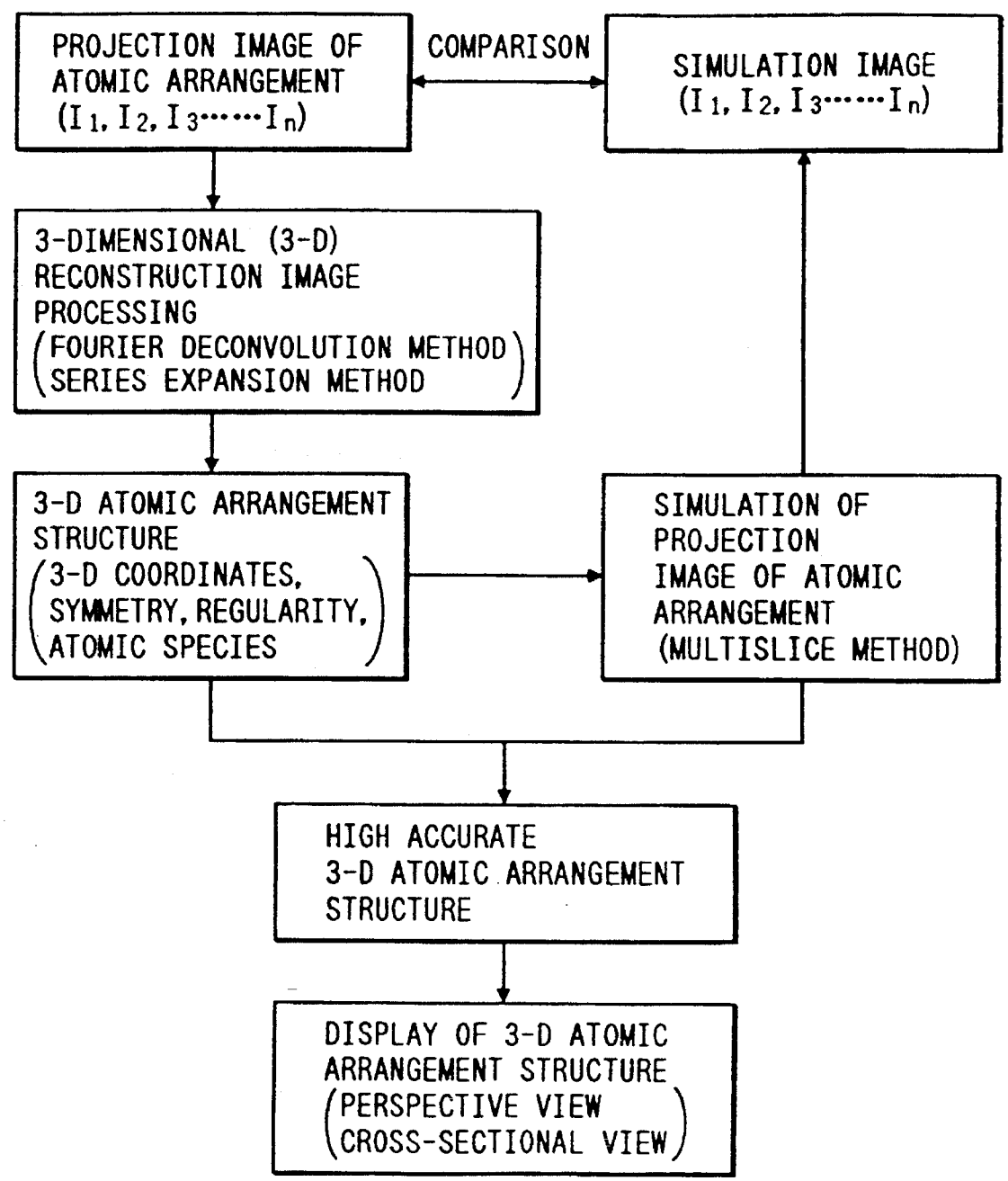
FIG. 4 is an explanatory view showing a process of constructing a 3-dimensional atomic structure by image processing of 2-dimensional atomic images observed at a variety of inclination angles θn of a specimen.

The image processing constructs a 3-dimensional structure of the atomic arrangement based on projection images of atomic arrangement 6 ($I_1$, $I_2$ to $I_n$) obtained at inclination angles ($\theta_1$, $\theta_2$ to $\theta_n$) respectively with a procedure shown in FIG. 4. The 3-dimensional structure of the atomic arrangement is displayed on a CRT of the computer 14. On the procedure, at first, 3-dimensional image processing is performed on the projection images of atomic arrangement 6 ($I_1$, $I_2$ to $I_n$) to identify 3-dimensional coordinates, the symmetry, and the regularity of the atoms. The atomic arrangement identified above are then combined with measurement data of atomic species to determine a 3-dimensional structure of the atomic arrangement of the specimen 19. The technique adopted for constructing the 3-dimensional structure is the same as that described on Page 15 of No. 6, Vol. 17, 1978 of Measurement and Control, a technical journal. The image processing software for constructing the 3-dimesional structure, which is capable of creating a 3-dimensional configuration based upon information obtained even from a range of possible inclination angles 0 to about 20 degrees of a specimen. For example, the softwares are Fourier deconvolution method and the series expansion method. The image processing software is executed by the computer 14 which selects one of the techniques in accordance with the amount of information to be processed. Based on data of the 3-dimesional structure of the atomic arrangement, a projection image of the atomic arrangement 6 is then simulated. Software used in the simulation applies a typical method such as the multi-slice technique. The simulated image is then compared to the observed image in order to confirm whether or not a projection image of the atomic arrangement 6 can be reproduced from the constructed 3-dimensional structure of the atomic arrangement. If the reproduction is impossible, the data of the 3-dimesional structure of the atomic arrangement is corrected to give another simulated projection image of the atomic arrangement 6. This operation is repeated until the simulated image matches the observed one. In this way, the accuracy of the 3-dimensional structure of the atomic arrangement can be enhanced. The 3-dimensional structure of the atomic arrangement determined as such is finally displayed on the CRT of the computer 14 as a squint image or a cross-sectional view seen from any desired direction.

The composition and bonding state of elements constituting the specimen 19 can be analyzed by measurement of a characteristic X-ray by the X-ray detector 15 and measurement of loss energy of transmitted electrons by the energy analyzer 16. A scanning tunnelling microscope is installed at the specimen preparation room 17 in which the thinning process of the specimen 19 is carried out by utilizing a field-evaporation effect that occurs when a field is applied to an area between a tip and the specimen 19. In this way, atoms are stripped off one by one. Accordingly, the thickness of the specimen 19 can be controlled in atomic-layer order without damaging the specimen 19 at all. By carrying out the operation to strip off atoms as such while observing the specimen 19 through the scanning tunnelling microscope, the structure of an infinitesimal portion of interest can be surely converted into a thin film with an accuracy at the atomic level. Since the thin-film specimen 19 is conveyed by the specimen transfer system 18 to a specimen observation room through a vacuum, the specimen 19 is neither contaminated nor oxidized. In the specimen preparation room 17, the specimen 19 can undergo manufacturing and fabrication processes such as the specimen cleaning and alteration using ion radiation and heating and the thin-film formation using evaporation and sputtering. Therefore, atomic structures in a variety of states can be observed. Furthermore, the specimen preparation room 17 can be removed from the electron microscope and connected to the actual thin-film equipment used in the semiconductor process. In such an arrangement, a specimen formed by the thin-film equipment is conveyed to the apparatus provided by the present invention in which the evaluation of its process conditions can be carried out.

As described above, the present invention allows the observation of the 3-dimensional atomic arrangement at a high resolution of higher than 0.2 nm The present invention also allows the analysis of atomic species. In addition, the present invention allows the composition and the bonding state to be measured as well. Point defects, impure atoms and their clusters which are difficult to examine using the conventional electron microscope can thereby be observed at a single-atomic level. Accordingly, the causes of ULSI devices' defects, thin film's formation conditions and the like can be evaluated at high accuracy. In the case of the conventional electron-microscope techniques, as many specimen samples as numerous observation directions have to be prepared in order to accomplish 3-dimensional observation. With the present invention, however, only a single specimen is required. As a result, the T. A. T. (turn-around time) of the evaluation process is substantially reduced as compared to that of the conventional techniques.

What is claimed is:

1. An instrument for 3-dimensional atomic arrangement observation comprising an electron gun, magnetic lenses for illumination, electron deflector coils and a specimen holder, said instrument comprising:

a specimen goniometer/tilting system having a driving means connected with said specimen holder;

an electron detector for observing a plurality of 2-dimensional atomic-arrangement images of a specimen upon application of a scanning electron beam with an atomic-level diameter;

means for compensating automatically a shift of specimen position induced by the specimen tilting; and a computer for executing control of said specimen goniometer/tilting system, said electron detector and said compensating means.

2. An instrument for 3-dimensional atomic arrangement observation according to claim 1, wherein said specimen goniometer/tilting system connected to said computer is capable of fine-controlling the inclination of said specimen by finding an amount of positional aberration due to said specimen inclination so that a structure of interest in said specimen is always held at the center of an observation area.

3. An instrument for 3-dimensional atomic arrangement observation according to claim 1, wherein said electron detector comprises a plurality of photosensitive devices arranged in a matrix configuration so that a range of scattering angles and scattering directions of scattered electrons used for formation of said 2-dimensional atomic-arrangement images being selected arbitrarily.

4. An instrument for 3-dimensional atomic arrangement observation according to claim 3, wherein said photosensitive device has a size of several micrometers or less.

5. An instrument for 3-dimensional atomic arrangement observation according to claim 1, wherein said computer comprises image-processing software for, when executed by said computer, storing said 2-dimensional atomic-arrangement images observed at each inclination angle of said specimen at an angular accuracy corresponding to the atomic distance and constructing a 3-dimensional atomic-arrangement structure using said 2-dimensional atomic-arrangement images.

6. An instrument for 3-dimensional atomic arrangement observation according to claim 5, wherein said image-processing software includes a program for, when executed by said computer, reconstructing an image of a 3-dimensional structure from a plurality of 2-dimensional projection images obtained by viewing said 3-dimensional structure from a variety of angles.

7. An instrument for 3-dimensional atomic arrangement observation according to claim 6, wherein said image-processing software includes a program for, when executed by said computer, constructing a cross-sectional image at any cross section of a 3-dimensional structure and a program for, when executed by said computer, constructing a squint view of a 3-dimensional structure as seen from any arbitrary direction.

8. An instrument for 3-dimensional atomic arrangement observation according to claim 1, wherein said computer comprises control software for, when executed by said computer, controlling said instrument.

* * * * *